United States Patent [19]

Russo, Jr. et al.

[11] Patent Number: 5,503,750
[45] Date of Patent: Apr. 2, 1996

[54] MEMBRANE-BASED PROCESS FOR THE RECOVERY OF LACTIC ACID BY FERMENTATION OF CARBOHYDRATE SUBSTRATES CONTAINING SUGARS

[76] Inventors: Lawrence J. Russo, Jr., 15000 Douglas Rd., Mishawaka, Ind. 46545; Hyung S. Kim, 10360 Hickory Hills Ct., Osceola, Ind. 46561

[21] Appl. No.: 131,458

[22] Filed: Oct. 4, 1993

[51] Int. Cl.$^6$ .................................................. B01D 61/58
[52] U.S. Cl. ........................... 210/641; 210/651; 210/259
[58] Field of Search ........................... 426/656; 210/639, 210/641, 650, 651, 259

[56] References Cited

U.S. PATENT DOCUMENTS

| | | | |
|---|---|---|---|
| 3,472,765 | 10/1969 | Budd et al. | 210/7 |
| 4,444,881 | 4/1984 | Urbas | 435/139 |
| 4,771,001 | 9/1988 | Bailey et al. | 435/139 |
| 5,068,419 | 11/1991 | Kulprathipanja | 562/580 |
| 5,250,182 | 10/1993 | Bento et al. | 210/641 |

OTHER PUBLICATIONS

"Adsorptive Purification of Carboxylic Acids" by Elizabeth E. Ernst and Donald W. McQuigg Paper #5ae at the AIChE 1992 national meeting, Separation Division preprints.
"Production of Lactic Acid from Lignocellulosic Biomass" by N. Padukone, S. Schmidt et al. Abstract only.
"Recovery of Lactic Acid by Adsorption: Resin Evaluation" by R. L. Evangelista and Z. L. Nikolov—Abstract only.

*Primary Examiner*—Frank Spear
*Attorney, Agent, or Firm*—Alfred D. Lobo

[57] ABSTRACT

A substantially continuous membrane separation process has been discovered in which the known benefits of a cell-recycle fermentor are unexpectedly enhanced because pH is controlled from 4.0 to 5.5 with a nitrogen-containing base. The ammonium lactate formed is not precipitated, allowing continuous removal of lactic acid so as to maintain a concentration of lactic acid about 12% by wt in the broth. When combined with recycle of UF retentate, operating this cell-recycle fermentor allows the build-up of a cell population in the range from above $5\times10^9$ CFU/ml to $5\times10^{10}$ CFU/ml, which population is much denser than one which can be produced with the specified pH control in a batch fermentor, after self-termination of the fermentation. This super-dense population of cells, In turn, not only accelerates production of lactic acid but also minimizes contamination by foreign cells. UF retentate is recycled to produce a specified high fluid velocity when the effluent stream is flowed over UF membranes used in the UF modules. The high fluid velocity at relatively low pressure produces a scrubbing action over the membrane surfaces which are therefore not fouled over long periods of operation. In a batch fermentation with pH control, when the fermentation is self-terminated the total lactic acid present is about 10% by wt (measured by HPLC), though free lactic acid is always <4%, and the live cell population is lower than $5\times 10^9$ CFU/ml because many cells die as pH drops.

20 Claims, 4 Drawing Sheets

| STREAM IDENTIFIER | 1 | 2 | 3 | 4 | 5 | 6 | 7 | 8 | 9 | 10 | 11 | 12 | 13 | 14 | 15 |
|---|---|---|---|---|---|---|---|---|---|---|---|---|---|---|---|
| STREAM NAME | HYDRA-SIEVE FEED | HYDRA-SIEVE SOLIDS | HYDRA-SIEVE FILTRATE | MF MEMB. FEED | MF RE-CYCLE | MF CONC. BLEED | MF PERM. | NF MEMB. FEED | NF RE-CYCLE | NF CONC. BLEED | NF PERM. | RO MEMB. FEED | RO RE-CYCLE | RO CONC. BLEED | RO PERM. |

MEMBRANE-BASED PROCESS FOR THE RECOVERY OF LACTIC ACID BY FERMENTATION OF CARBOHYDRATE SUBSTRATES CONTAINING SUGARS

BACKGROUND OF THE INVENTION

The present invention is directed to the production of lactic acid directly from a bioconversion reactor ("bioreactor" or "fermentor") broth made in a process for the fermentation of saccharified grain mash or molasses by a homofermentative strain of microorganisms which convert fermentable free sugars in the broth to lactic acid. The term "broth" refers to a submerged culture fermentation broth in a fermentor, which broth contains the mash of ground grain which is saccharified before it is fermented to yield lactic acid as the predominant acid, and by-products. The term "fermentable free sugars" refers to pentoses and hexoses, but mainly hexoses, present in jet-cooked and saccharified grain mash. By "lactic acid" we refer to all forms of lactic acid molecular weight ("mol wt" for brevity) 90.08, namely 'levorotatory' L(+), 'dextrorotatory' D(−), or racemic L(+)D(−) lactic acid, and reference to lactic acid herein refers to the foregoing individually and severally, unless stated otherwise.

The problem to be solved is: how to produce a high yield of lactic acid from the fermentor broth of a commodity grain until essentially all nutrient is used up, and to make the separation of essentially pure lactic acid economically feasible without precipitation of a salt of lactic acid (e.g. calcium lactate). The term "essentially pure" refers to recovered lactic acid having less than 5% by wt of low mol wt contaminants produced during a fermentation even if "corn thin stillage" ("thin stillage" for brevity) or "steep water" is used as a nutrient, the contamination being due to low mol wt compounds such as byproduct acetic acid and glycerol which are rejected together in reverse osmosis ("RO") modules. If neither thin stillage nor steep water is used, lactic acid produced may be 95% pure or higher.

The process of this invention is especially beneficial if it is operated in conjunction-with a fermentation plant producing ethanol from corn or sweet sorghum. In such a plant, thin stillage and steep water are waste streams, which are found to provide an exceptionally nutritious feed supplement for Lactobacilli which ingest the fermentable sugars present in corn mash, molasses, tapioca, potatoes and the like. The live microorganisms convert the sugars to lactic acid.

Thin stillage and steep water are produced in the dry milling and wet milling processes, respectively, for the production of ethanol from saccharified corn or sweet sorghum. To our knowledge, no prior art fermentation of grain mash, specifically corn or sweet sorghum mash, to produce lactic acid, has used either thin stillage or steep water as a nutrient. Of course, if either is unavailable there would be no over-riding reason for exploring their value as nutrients in this process. We use a portion of either by-product, typically in a minor proportion (less than 50%) preferably from 5% to 35% by weight (wet basis) of the fermentor's contents, in fermentations in which there is no objection to the small amount of glycerol introduced with the thin stillage. All percentages by weight (wt) given herein are on a wet basis unless specifically stated otherwise.

This process uses conventional unit operations which have been found, in combination, to be surprisingly result-effective. The process may be operated either in a "batch mode" with a batch fermentor; or, in a "continuous mode" with a cell-recycle fermentor. The "continuous mode" which is preferred for the operation of a plant, is a combination of a "continuous batch mode" with a "continuous feed and bleed".

In the batch mode, there is no feed flow into the fermentor containing fermenting broth and saccharified mash, and the entire contents of the fermentor are allowed to ferment until the fermentation is substantially self-terminated. The batch process is favored for ease of operation and freedom from possible contamination of the broth because a fresh charge of mash is freshly inoculated for each fermentation. Preferably, plural batch fermentors are operated in tandem to avoid the lag time due to waiting repeatedly for a fermentation to be self-terminated in a single fermentor.

The continuous process is favored for economics since, except for the initial fermentation, there is no lag time for production of the lactic acid, and labor and other overhead costs are lower. In the "continuous batch mode" also known as the "modified batch mode" only the 'retentate', also termed 'concentrate', is returned to the fermentor while permeate containing the lactic acid is withdrawn, and fresh feed is continuously supplied to the fermentor, to maintain a constant level in the fermentor. During continuous operation, returning retentate to the fermentor gradually increases the concentration of rejected undissolved solids in it, and a portion of the contents of the fermentor are purged from time to time. Because the pH is controlled within a narrow range in this novel process, returning only the retentate results in the operation of a cell-recycle fermentor. The concentration of cells in the fermentor is increased, but that of lactic acid is not permitted to exceed 3% by wt (without pH control), above which cells known today have difficulty staying alive, and do not grow noticeably. Though the principle of using a cell-recycle fermentor to increase cell concentration, that is CFU/ml (colony-forming units/ml), is known, one could not predict the effects of using the principle under the conditions of this process. Because of the effects of doing so, described in detail hereafter, the production and recovery of lactic acid is unexpectedly highly efficient.

Thin stillage typically contains a substantial concentration of water-insoluble ("suspended") solids, as well as "dissolved" solids, only the solids larger than about 15 μm (micrometers or microns) in nominal diameter having been removed. If thin stillage is not used as a feed component to the fermentor, comparable nutrients are typically required to be added to maintain the same healthy state of cell growth. The disadvantage of using thin stillage is that the glycerol therein stays with the lactic and acetic acids, decreasing the purity of the lactic acid. Since thin stillage is discharged from a centrifuge which separates relatively large, water-insoluble solids in "whole still-age" leaving the thin stillage, some solids larger than 500 μm are likely to remain with the thin stillage and, for reliability, it is desirable to prefilter broth withdrawn from the fermentor through a fine screen in the mesh size range from about 250 μm–500 μm, preferably 250 μm mesh size, to remove the "heavy solids" from the mash before introducing the broth into an ultrafiltration ("UF") zone containing module(s) of ultraporous tubular membranes with pores no greater than 0.375 μm.

If it is desired to separate the glycerol from the lactic acid in the product stream obtained as the retentate from a RO (reverse osmosis) zone, the glycerol is separated by known separation means, for example, ion exchange resins, as is the acetic acid, if it is to be separated. Where glycerol is not detrimental, it is left in the lactic acid, irrespective of whether the acetic acid is separated.

In the parent application, lactic acid was recovered as a by-product of a fermentation process in which corn was used to produce ethanol. Evolving economics, now skewed by a heightened awareness of the benefits of using a renewable resource combined with a topical demand for lactic acid, led to exploring the fermentation of corn and sweet sorghum, specifically, to yield lactic acid as the main acid product.

Lactic acid is not nearly as large a commodity biochemical as it would be, if only it could be produced more economically than it is today. It is now used in specialty chemicals, as a food acidulant and flavoring, and in pharmaceutical products, but several times as much could be used in textiles, and for other industrial applications such as for biodegradable synthetic resinous materials if lactic acid was readily available in volume. To date, the yearly increase in production of lactic acid has been due to its use in food and pharmaceutical products but it is expected that 0.5 billion Kg of lactic acid will now be used.

Lactic acid is now manufactured by one of several synthetic and fermentative methods, for the reason that sources of free sugars, such as molasses, potatoes or starch, for mono- and disaccharides, are not only less costly to purchase (alas, not "free") but also are renewable. Further the processing costs for fermentation processes are lower than those for synthetic processes, particularly those based on petroleum-based raw materials. Free sugars include monosaccharides such as glucose, fructose, galactose, and disaccharides include sucrose and lactose.

Certain homofermentative strains producing essentially only lactic acid are preferred, such as *Lactobacillus delbrueckii, L. casei, L. xylosus, L. plantarum, L. acidophilus*, and *L. bulgaricus*. The first and second strains, namely *L. delbrueckii* and *L. casei* consume free 6-C sugars in corn mash and sweet sorghum mash such as glucose, sucrose, and fructose, but do not consume lactose. Other species consume lactose and galactose in addition to the other sugars and the choice of species, or a mixture of species, depends upon the particular raw material to be used. Whichever species, or mixture of species, chosen for use, the fermentation product will contain a substantial concentration of suspended solids, as well as "dissolved" solids.

In the past, recognizing the economic attraction of using a fermentation process for lactic acid, those skilled in the art have used various types of processes involving solvent extraction, adsorption and desorption, electrodialysis and combinations of the foregoing to arrive at an economically effective process. See *Adsorptive Purification of Carboxylic Acids* by Elizabeth E. Ernst and Donald W. McQuigg, Paper #5ae at the AIChE 1992 National Meeting, Separations Division preprints, First Topical Conference on Separation Technologies: New Developments and Opportunities, Nov. 2–6, 1992, Miami Beach, Fla. The relatively high price of lactic acid in the marketplace is evidence that producing lactic acid in volume, is difficult. It was therefore particularly noteworthy that what appeared to be the simplest and most straightforward separation process, namely multiple filtrations in series, was bypassed.

This reluctance to utilize multiple filtrations may have been inoculated by experiments reported in an article titled "Lactic Acid Production by Electrolysis Fermentation Using Immobilized Growing Cells" by Hongo, Nomura and Iwahara in *Biotechnol. & Bioeng.*, 30, 788–793 (Oct 1987) in which they used a broth containing cells in membrane-equipped electrodialysis tanks and found that the membranes were fouled despite the cells being dead. Though it was known that cells could be removed in a "UF" zone, Datta in U.S. Pat. No. 4,885,247 deemed the process was impractical because removing cells by UF is expensive, particularly since the concentration of lactic acid in the fermented broth was generally no higher than 10% by weight on a wet basis (see e.g. U.S. Pat. No. 5,068,418 to S. Kulprathipanja, Table, col 3, line 60). Datta did not comment on the problem of maintaining live cells under relatively high fluid pressures and high shear energy to which the broth is subjected in a conventional pump which pumps the broth to be ultrafiltered.

Long before Datta's disclosure, it was known that a continuous, high productivity, cell-recycle, activated sludge digester as disclosed in U.S. Pat. No. 3,472,765 to Budd et al, could be used to reduce the cost of bioconversion of sewage by increasing volumetric productivity based on continuously separating biomass from the contents of the digester and recycling the biomass to the digester, if the appropriate membranes could be provided to make the necessary separation. However, despite the fact that Pseudomonas cells predominantly present in activated sludge in the size range from 1 μm to 2 μm are easier to separate from the water than Lactobacilli which are smaller (about 1 μm long, 0.5 μm in diameter), Budd et al teach directly flowing the withdrawn activated sludge to a RO and UF membrane from which the retentate is recycled to the digester. The RO membrane would, of course, also provide the UF function, so that this UF function would be redundant.

There is no indication whether the membranes would be blinded or damaged under specified conditions, and, if not, the conditions under which they would not be. Nor did Budd et al consider that only an insignificantly small fraction, if any, of live cells leaving the digester might survive the pressure required to produce any permeate through any UF or RO membrane. Clearly increasing the concentration of dead cells in the digester at the expense of those left alive, is not calculated to improve the efficiency of the digestion process.

The '765 patent gives no consideration to criteria which would govern the acceptable performance of the UF or RO membranes, so that one can derive no suggestion that only tubular UF membranes are likely to give acceptable results, and such results would be derived only if the activated sludge leaving the reactor was to be pumped over the tubes at a velocity in excess of 3 m/sec, preferably from 5–10 m/sec, but not high enough to kill more than 25% of living cells in the stream being pumped, preferably no faster than 30 m/sec, at relatively low pressure.

Specifically, since the '765 patent expressly teaches that the contents of the activated sludge fermentor are pumped through a withdrawal conduit to a housing having a flat plate RO membrane "selected so that they perform a reverse-osmosis and ultrafiltration separation operation wherein the biological life is retained on the feed side of the membrane", (see col 3, lines 68–70) without any suggestion that a UF separation be carried out first, it is clear Budd et al did not recognize the criticality of dealing with the solids in the broth, first, with a tubular UF filter, then, filtering the UF permeate in a RO filter, irrespective of the RO filter's configuration. Nor did they recognize that a preferred combination of a tubular UF and a NF filter of any configuration, would reliably produce a permeate essentially free of suspended solids, making it practical to filter the permeate from the NF filter in a RO zone. Further, though Budd et al sought a permeate essentially free of suspended solids they chose a UF or RO membrane to provide it, and did not recognize that only the latter (RO) could. Moreover, their choice of a UF membrane negates the probability that they could have appreciated the criticality of the relationship of cell size to pore size, and suggests they neither knew nor experienced the severity of the problem which existed. Thus, they found no need for any intermediate separations. In contrast, since the thrust of this invention is to provide lactic acid in volume, efficiently, it not only requires that there be multiple separations, but also that the pore size of the first UF ultraporous zone be critically related, that is, "cell-matched" to the diameter of the cells, as defined herebelow.

Still further, Budd et al failed to recognize that the pitfalls of filtering the cell-containing sludge, could only be avoided by using a cross-flow tubular UF means having a pore size in the range from about one-fourth (0.25), preferably one-half (0.5), the average nominal diameter of a cell, up to no more than three-fourths (0.75) that diameter. It is only with this combination of "cell-matched" ultraporous means in cross-flow filtration that our process gives acceptable recovery of cells and permeate. Even if it had been appreciated that a stream essentially free of suspended solids had been sought for the RO zone, and Budd et al had used a membrane with very small pores, smaller than 0.1 µm, the filtration would be too inefficient to be practical.

The term "cross-flow" entails the flow of three streams—feed, permeate and retentate. In contrast, a "dead end" or "depth" filter has only two streams—feed and filtrate (or permeate). In cross-flow, feed flows through membrane channels, either parallel (or tangential) to the membrane surface, and is separated into a retentate (and/or recycle) stream and a permeate stream. The recycle stream retains all the particles and large molecules rejected by the membrane. The feed/recycle stream mixture flows through filter channels and may be totally recycled to the membrane module in which the recycle is generated, or partially removed from the system as reject (retentate). The key to maintaining an efficient membrane is to flow broth, at a sufficiently high velocity, parallel to the membrane surface to create shear forces and/or turbulence to sweep away accumulating particles rejected by the membrane.

To date, a favored method for the separation of lactic acid is to precipitate the calcium salt. The resulting calcium lactate is filtered to remove heavy metals and some organic impurities. The regenerated lactic acid is separated from precipitated $CaSO_4$ (say), e.g., by filtration, and the resulting crude lactic acid further purified by carbon treatment and sodium ferrocyanide to remove additional organic impurities and heavy metals, respectively. After filtration, the lactic acid is contacted with an ion exchange resin to remove trace ions. It is immediately evident that this separation and purification process is complex and lactic acid purity in excess of 99% is difficult to obtain.

As indicated at the outset, it was the goal to replace the prior art process with an effective membranous separation of lactic acid from a suitable broth, which instigated the search for a "membrane solution" to the problem of separating lactic acid-efficiently. Such a separation was conceptually incited by a membranous separation of lactic acid from a fermentation broth to produce ethanol, described in the parent case. Except the broth is now generated with predominant strains of L. casei and L. delbrueckii and the like, which are gradually mutated by being recycled, to tolerate lower and lower pH levels in the range from pH 4.0 to 5.5, without sacrificing the production of lactic acid.

Because lactic acid is present in prior art broths in relatively low concentration, less than 8% on a weight basis (weight lactic acid / weight of broth or "w/w") even with pH control, recovering the lactic acid by filtration alone, has been such a technically unpromising and predictably unrewarding task, that to date, there has been no attempt, in a commercial process, to explore a filtration-only separation process. There is no record in the prior art of a suggestion as to how or why a filtration-only membrane process might be imminently operable; nor is there any suggestion that such a process will have the ability, economically to recover lactic acid from a fermented broth of grain.

Besides lactic acid among the dissolved solids, are numerous by-products since, generally, only the solids larger than 1 µm in nominal diameter having been removed by microfiltration ("MF"). Dissolved solids include cell-compatible buffers and growth-enhancing nutrients, carbohydrates, amino acids, proteins and naturally occurring salts, and products of the bioconversion of sugars, all together referred to as "by-products". By "cell-compatible" buffer is meant one that improves production of lactic acid relative to an unbuffered broth, without stunting the growth of the active bacteria. The concentrations of byproducts ranges from about 100 ppm to 2 percent by weight of fermented broth, depending upon where in the process the concentration is measured. These by-products must be separated from the broth, to yield essentially pure lactic acid. To do so is neither simple nor inexpensive.

The reason for the failure to provide an economical process appears to have been a widespread misappraisal and misjudgment of the ability of a membrane means to make a critically important separation in the UF filtration step; and, the failure to realize that the relatively low mol wt of lactic acid relative to other by-products, fortuitously allows its separation and recovery from an aqueous stream containing proteins and relatively high mol wt ($C_{10}$–$C_{24}$) fatty acids, provided the "right" membranes are used in the "right" combination.

Further, since it could be calculated that under the most desirable conditions achieved in the prior art, the overall permeate recovery of a fermentation broth in a UF, NF or RO module appeared to be unattractive, there was no motivation to probe the advantages of a process in which the broth was ultrafiltered, then nanofiltered, then RO filtered, under particularly specified conditions which provide at least 50% recovery in each step. There was little reason to suspect that such a membrane process could be economical. There was less reason to suspect that a membrane process could avoid or overcome the fouling problems endemic to such processes, particularly since it is well known that such problems are the basis for disproportionately large operating and maintenance costs.

In the context of this process it is important to note that the term UF refers to a membrane having pores no larger than 0.375 µm, this being 0.75 times the ≈0.5 µm diameter of a generally rod-shaped Lactobacillus, or 0.75×0.5 µm=0.375 µm and if one was to use a microfiltration (MF) membrane having a microporous pore size of 0.4 µm, rod-like cells partially inserted end-wise in the pores, would effectively blind the pores and the microfiltration is inefficient. When so inserted, the trapped cells, or portions thereof, defy being dislodged even with back-pulsing the membrane tubes.

The pores in a conventional MF membrane are generally accepted as being in the size range from about >0.2 µm, ranging up to 10 µm. A MF module is typically used to remove finely divided suspended solids much larger than cells, along with those cells which may be closely associated with the removed solids. The high recovery rate in our process is based, in the main, upon the discovery that a pore size no larger than 0.375 µm, preferably 0.2 µm, produces a cell-free permeate, and a membrane with this pore size resists blinding, fouling and damage. The productivity of a fermentation process with UF membranes having a smaller pore size than 0.1 µm is inefficient and uneconomical.

A NF membrane being semipermeable and non-porous, provides a subsequent intermediate separation based both on mol wt and ionic charge. Mol wt cut-offs for non-ionized molecules are typically in the range from 150–1000 Daltons, referred to as "lights". For ions of the same mol wt, membrane rejections will increase progressively for ionic charges of 0, 1, 2, 3 etc. for a particular membrane because of increasing charge density (see "Nanofiltration Extends the Range of Membrane Filtration" by Peter Eriksson, *Environmental Progress*, Vol 7, No 1, pp 58–59, February 1988). The effectiveness of the NF semipermeable membrane means in this process derives from the presence of a large portion of the lactic acid in the UF permeate being present as lactate anions and $H^+$ cations in equilibrium with non-ionized lactic acid.

A RO membrane is also semipermeable and non-porous, but requires an aqueous feed to be pumped to it at a pressure above the osmotic pressure of the dissolved substances in the water. Because an RO membrane can effectively remove low mol wt molecules<150 Daltons, and also ions from water, RO membranes are commonly used to demineralize water (e.g. for pretreating boiler feedwater, and recovering potable water from brackish water or sea water). An RO membrane is ideally suited for making the separation of low mol wt lactic acid $HOOC—CH(CH_3)—OH=90$, from higher mol wt components in the NF permeate.

SUMMARY OF THE INVENTION

A substantially continuous process has been discovered in which the known benefits of a cell-recycle fermentor are unexpectedly enhanced because of controlling pH in the range from 4.0 to 5.5 with a nitrogen-containing base, most preferably ammonium hydroxide, allows continuous removal of lactic acid so as to maintain a surprisingly high concentration of acid about 12%, preferably about 6% by wt in the broth, optionally supplemented with thin stillage or steep water, and optionally buffered with protease. When combined with recycle of UF retentate, operating this cell-recycle fermentor allows the build-up of a cell population in the range from above $5 \times 10^9$ CFU/ml to $5 \times 10^{10}$ CFU/ml, which population is much denser than one which can be produced with the specified pH control in a batch fermentor, after self-termination of the fermentation.

In a self-terminated fermentation with pH control, the total lactic acid present is about 10% by wt (measured by HPLC), though free lactic acid is about 3%, always<4%, and the population is lower than $5 \times 10^9$ CFU/ml. A higher "super-dense" population of cells is obtained by the continuous removal of lactic acid which maintains a low-free-acid environment conducive to the virulent growth of the bacteria, along with the nutritional value of the nitrogen-containing base used to control the pH; this super-dense population of cells, in turn, not only accelerates production of lactic acid but also minimizes contamination by foreign cells; and since the UF retentate is recycled, a relatively large portion of the broth in the fermentor may be withdrawn as a fermentor effluent stream, sufficient to produce a specified high fluid velocity when the effluent stream is flowed over UF membranes used in the UF modules. The high fluid velocity, preferably from 5–10 m/sec, at relatively low pressure less than 1140 kPa (150 psig), produces a scrubbing action over the membrane surfaces which are therefore not fouled over long periods of operation.

The process may be operated as a batch process by maintaining a pH in the range from 4.5 to 5.5 with addition of a nitrogen-containing base, preferably ammonia, so as to generate ammonium lactate in solution, and to continue the fermentation until the concentration of lactic acid, measured by HPLC for all free lactic acid and lactate ions, is in the range from 8 to about 15%, preferably exceeds 9%, and typically is in the range from 10–12%.

It has also been discovered that "corn thin stillage" and "steep water" obtained as by-products in the fermentation of corn using the dry milling and wet milling processes, respectively, are excellent supplemental nutrients for live microorganisms adapted to ferment a carbohydrate substrate containing fermentable free sugars to yield lactic acid and acetic acid.

It has further been discovered that protease, which is an enzyme that catalyzes the hydrolytic breakdown of proteins, added to the broth, generates amino acids and peptides in situ; and, the amino acids and peptides function as a cell-compatible buffer providing readily assimilatable nutrients. Thus, for no known reason, protease functions as a lactic acid "booster" which boosts not only the net amount of lactic acid produced by *Lactobacillus delbrueckii, L. casei, L. acidophilus, L. leichnanii, L. bulgaricus* and the like, but also the rate at which the concentration of lactic acid is increased until the fermentation is self-terminated, thus greatly shortening the normal cycle in a batch fermentation.

It has also been discovered that lactic acid produced in a fermentor may be efficiently recovered in a process comprising three processing sequences: a first, an intermediate, and a final processing sequence. The first sequence comprises an initial fermentation step and a subsequent large-solids-removal (heavy solids) step; the second sequence comprises an initial UF step and a subsequent NF step; and the final sequence comprises an initial RO step and, optionally, a subsequent purification step.

In the intermediate sequence, the combination of the initial UF step and the subsequent NF step is critical to the effectiveness of this particular process, the criticality of operating the NF step being predicated upon that of the prior UF step.

It is essential that, in the NF step, the feed to the NF zone be not only cell-free but also essentially free from suspended solids, that is, the NF feed contain less than 10 ppm, preferably less than 5 ppm of suspended solids, or a "silt density" or "fouling index"<5. Such a suspended solids-free feed is provided by the initial UF step of the intermediate sequence, in which a UF permeate is removed from a UF zone housing one or more modules fitted with tubular porous membranes having a pore size in the range from 0.1 µm to 0.375 µm. This UF permeate when filtered in the NF zone of the subsequent NF step provides a NF permeate which can be filtered in the final purification zone. The NF zone comprises one or more RO module(s) from which the recovery of lactic acid in the retentate of the RO module(s) is excellent.

Therefore, in the initial step of the first processing sequence, lactic acid is produced in a fermentation broth containing fermentable free sugars. The lactic acid is produced in a concentration in the range from 5%–15% by weight (wet basis, 5–15 gm lactic acid/100 ml of broth), more typically in the range from 6%–10% with control of pH by neutralization with NH$_4$OH. This broth is pretreated in the subsequent step of the first processing sequence to remove relatively heavy solids>500 µm, preferably>250 µm, to produce a broth having essentially no solids>500 µm, preferably no solids>250 µm.

This essentially solids-free broth is then ultrafiltered in the tubular UF membrane zone to provide the desired UF permeate with at least 80% recovery of the lactic acid in the permeate, preferably greater than 90%, to yield a UF retentate having a total solids conc in the range from at least 15% to as high as 35%, preferably 20%–30%. The combined concentration of lactic acid and by-products in the UF permeate is typically in the range from 1–4% by wt, and depends upon the amount of lactic acid produced in the fermentation process, the higher the concentration, the higher the recovery. This UF permeate produced can then be efficiently filtered in the NF zone having one or more NF modules which are continuously operable for a long enough period to make the NF filtration practical. The combined concentration of lactic acid and by-products in the NF permeate is typically in the range from 2–10% by wt, and again depends upon the amount of lactic acid produced in the fermentation process. The recovery of lactic acid in the NF permeate is preferably in the range from about 80–95% in a single stage NF zone, and may be as high as 98% if a two-step NF filtration is used, or if diafiltration is used in combination with the NF modules.

Upon filtration in the RO zone, the NF permeate produces a RO retentate containing the lactic acid, typically in the range from 5 to 30% by wt. The minimum yield of lactic acid recovered in the RO retentate in an economical plant operation is about 40% based on the conc of lactic acid in the broth. The recovery is preferably in the range from about 55–85%, and may be as high as 95% if a two-step NF filtration is used, or if diafiltration is used in combination with the NF modules, and there is essentially no glycerol in the broth.

In general, the higher the concentration of lactic acid in the broth, the better the recovery. Note that the conc of lactic acid, acetic acid and glycerol (if thin stillage or steep water is used as a nutrient) in the UF permeate is substantially independent of UF recovery because there is essentially no rejection of any of these acid and glycerol components by an ultraporous membrane in the specified 0.1 µm–0.375 µm range.

Further, the UF membrane in the aforesaid pore size is necessarily tubular because a spiral wound UF membrane in this size range is too-readily fouled. The most preferred tubular UF membrane has a pore size ≈0.2 µm, and separates all cells and particles smaller than 0.2 µm, and, soluble materials based on mol wt, typically in the range from 1000–200,000 Daltons, referred to as "heavies" (not heavy solids). Essentially all solids smaller than 0.2 µm, most in the range from 0.05 µm–0.1 µm, are efficiently rejected in the NF zone.

Still further, in the continuous process, the retentates of (i) "heavy solids">250 µm from the UF zone, and of (ii) "heavies">200,000 Daltons from the NF zone, are both returned to the fermentor, thus utilizing the sugars in these retentates to feed the fermentation reaction, and to minimize waste of sugar. The permeate of deionized water from the RO zone is also recycled to the fermentor, though it need not be, if another source of contaminant-free water is available. Since the NF permeate now contains components which are easily separable in the RO zone, the RO separation of lactic acid, and such small amounts of glycerol and acetic acid as may be present, is efficiently effected.

It is found that the super-dense cell population in the range from above $5 \times 10^9$ to about $5 \times 10^{10}$ obtained in a cell-recycle fermentor with controlled pH, optionally with a buffered broth, cannot be obtained in a batch fermentor in which there is no recycle and no removal of lactic acid while the fermentation is in progress, despite identically controlling the pH of a similarly buffered broth. The increased productivity of lactic acid due to a super-dense cell population in a substantially closed system using a continuous cell-recycle fermentor with controlled pH in the range from 4.0 to 5.5, also helps to guard against broth contamination over a period of many cycles, because substrate and inoculum are added to the fermenting broth under steady state operating conditions, and only product lactic acid and a purge stream are withdrawn.

BRIEF DESCRIPTION OF THE DRAWING

The foregoing and additional objects and advantages of the invention will best be understood by reference to the following detailed description, accompanied with schematic illustrations of preferred embodiments of the invention, in which illustrations like reference numerals refer to like elements, and in which:

FIG. 1B identifies the streams.

DETAILED DESCRIPTION OF PREFERRED EMBODIMENTS

Lactic acid, a large portion of which is ionized at a temperature in the range from about 30° C. to 45° C., is recovered from the broth preferably at from 35° C. to 42° C., by a combination of filtration steps. The purity of lactic acid recovered depends upon the nutrients used for growth of the microorganisms used in the fermentation. The temperature of the fermentation determines that a large proportion of the lactic acid is ionized, and the ionic species of lactic acid are found to make separation of lactic acid from the broth, unexpectedly effective, so long as the separation is effected in a series of membrane separation means which at the very least, requires a combination of three filtration zones operating in series, including a first UF zone with a UF membrane having a pore size no greater than about three-fourths (0.75 times) the smallest dimension of a single colony forming unit or CFU, or living microorganism (hence referred to as "cell-matched"); a second NF zone with a semipermeable NF membrane; and, a third RO zone, with a semipermeable RO membrane.

The following recipe is for a fermentable broth in which thin stillage is used as a supplemental nutrient. The ingredients of the mash are as follows:

| Ingredient | Range, % by wt (wet basis) |
| --- | --- |
| Mashed corn | 5 to 25 |
| Yeast Extract | 0.05 to 0.8 |
| Buffers | 0.2 to 0.8 |
| Thin stillage | 2 to 8 |

An analogous fermentation product may be used, which product is obtained from the submerged culture fermentation of molasses, potatoes or, especially, starch provided by other grains, by bioconversion using *Lactobacillus delbrueckii, L. bulgarcius* or *L. leichnanii*, or any other microorganism which generates lactic acid. The fermentation product will have a composition exemplified by:

|  | wt. % (wet basis) |
| --- | --- |
| Lactic acid | 2.5 to 15 |
| Acetic acid | ≈1 |
| Carbohydrates | 3–18 |
| Fats | 1 to 5 |
| Cellulose | 2 to 10 |
| Minerals | ≈1 |
| Naturally occurring salts | ≈1 |

The carbohydrates are mainly glucose, xylose and arabinose; the amount of lactic acid in the broth will depend upon whether the fermentor is operated in a batch mode, when the lactic acid will not exceed about 12%, or in a continuous mode when the lactic acid will not exceed about 5%, preferably 3%; the naturally occurring salts may include those of K, Na, Ca, Mg and P which are introduced with the feed. Less than about 0.5% ethanol may be present in the continuous mode if there is some ethanol in the mash obtained. There could also be some ethanol present if the sterilization of the mash in a batch mode is done under pressure and such little ethanol as may be present, remains in the broth. The unknowns will include, other than dextrose and DP3, e.g., DP2, plus other unidentified saccharides, amino acids and proteins. The composition of the feedstock will vary from that given above depending upon what is chosen for operation.

The separation of lactic acid, particularly through the NF membranes (the UF membrane is not affected as much), can be enhanced significantly by adjusting the pH of the feed in the range from 4.5 to 5.5 which is above the ionization constant of lactic acid. The ionization constant pKa of lactic acid is 3.86, *Handbook of Chemistry & Physics*, 53rd Edition, 1972–3, CRC Press, and, therefore, the pH of the lactic acid feed and the adsorption zone should be well above it.

In aqueous solution, nonionized lactic acid exists in equilibrium with lactate anions and hydrogen ions. This is shown in the following equation where the acid dissociation constant, pKa of lactic acid at 100° C. is 3.86.

The equilibrium point of lactic acid dissociation can be shifted by varying the concentration of lactic acid, the lactate anion or the hydrogen cation, and it is preferred to shift the point in favor of a large proportion of lactate ions.

The amount of nonionized lactic acid and ionic species, H cations and lactate anions, present in the broth is based on the lactic acid equilibrium at the operating temperature of the fermentor. The ratio of lactate ions to nonionized lactic acid affects the rate at which both, the nonionized lactic acid as well as the ions travel through the UF and NF membranes, hence the speed of filtration. The ratio does not affect the overall recovery of the lactic acid. However, the higher the temperature, the higher the flux and the greater will be the efficiency of lactic acid recovery at a pH in the range from 4.0 to 5.5.

Essentially pure lactic acid, at least 95% pure, is recovered from the process, the remainder being mainly acetic acid, if the mash is not diluted with corn thin stillage or steep water. If either a thin stillage or steep water stream is added to the fermenting mash for the new-found nutrient value of either stream, glycerol present in the stream is an additional contaminant, though it is present in an amount<0.5% by wt which is in an amount comparable to the<0.5% by wt of acetic acid present. Typically, with addition of 25% thin stillage containing about 0.8% glycerol, the glycerol concentration in the lactic acid is about 0.2% and the acetic acid is<0.1% by wt.

The pH of the broth, during fermentation, is controlled by the addition of ammonium hydroxide or other nitrogen-containing organic compound which results in salts of monocarboxylic acids which are soluble in the broth. Rather than forming a precipitate of a salt from which lactic acid is then derived by acidifying the salt, as is done in prior art processes, it is essential that the lactic acid be held in solution. Neither a mineral nor organic acid is necessary to acidify the broth; and there is no advantage to adding any other inorganic base (other than $NH_4OH$), e.g. NaOH, to control pH.

A typical, preferred charge to the fermentor includes from 5 to 25% by wt of mashed corn, from 2 to 8% by wt of thin stillage, from 0.05 to 0.8% by wt of yeast extract, and from 0.2 to 0.8% by wt of buffers. If no thin stillage is used, its nutrient value is replaced by a combination of cell nutrients which include one or more of the following: discharges from yeast, mold and bacterial fermentations, e.g. whey.

The concentration of free sugars in the aqueous phase ranges from 3.5 to 17.5% depending upon the type of corn or sweet sorghum used and include mainly glucose, xylose and arabinose. The fermenting broth also contains from about 1 to 5% fats, from about 2 to 10% cellulose in the form of cellulose, hemicellulose and lignin, and less than 1% by wt of minerals.

Upon reaching a steady state in the fermentor when the desired cell concentration is in the range from $3 \times 10^{10}$ to $5 \times 10^{10}$ CFU/ml, and the concentration of lactic acid in the broth is in the range from 8 to 10% by wt, the lactic acid is continuously removed as soon as it is produced, so that there is no build-up of lactic acid in the fermentor.

The broth discharged from a fermentor in which lactic acid is generated from molasses, corn, sorghum or other saccharified grain mash rich in free sugars and relatively large insoluble solids, is most preferably separated by a 0.2 µm tubular UF membrane without blinding or fouling the membrane, into a permeate stream in which not only essentially all the insoluble portion of the broth, including insoluble proteins>0.1 µm is removed as retentate, but also at least 50% of solubles having a mol wt>$2\times10^5$ Daltons, including dissolved proteins in the broth. Yet a permeate recovery of at least 80%, preferably at least 90%, is maintained. In a subsequent NF second step, the UF permeate from the UF zone is further separated to produce a permeate recovery of more than 70% with a rejection of less than 30% of the lactic acid, preferably less than 20%. Essentially all molecules larger than lactic acid are removed in the NF retentate.

The economic attraction of this fermentation process for recovery of lactic acid is that the high velocity>3 m/sec over the membranes in the tubular UF module minimizes fouling whether the fermentation is run in the batch mode or the continuous mode. At such fluid velocity the UF membrane defies being blinded, damaged or fouled over a period of at least a month when the broth from the cell-recycle fermentor contains at least 30 gm of lactic acid per liter of broth, in equilibrium with a large concentration of lactate and $H^+$ ions. The relatively low pressure in the range from about 5 atm (atmosphere) to 10 atm of the pump discharge neither damages the membrane, nor kills the cells. The broth is maintained at a pH in the range from 4.0 to about 5.5, preferably about pH 5, by addition of $NH_4OH$, with cells in a concentration in excess of $3.0\times 10^{10}$ cells/ml. Minimal fouling, with a rejection of at least 90% of cells and less than 10% lactic acid, by the tubular UF membrane, in turn, allows depletion of the lactic acid in the fermentor quickly. UF permeate flowed to the NF module is unexpectedly efficient because it is essentially free from suspended solids, and in turn, this efficiency makes it possible to use RO membrane modules which allow an unexpectedly high recovery of lactic acid.

Figures 1, 1A:
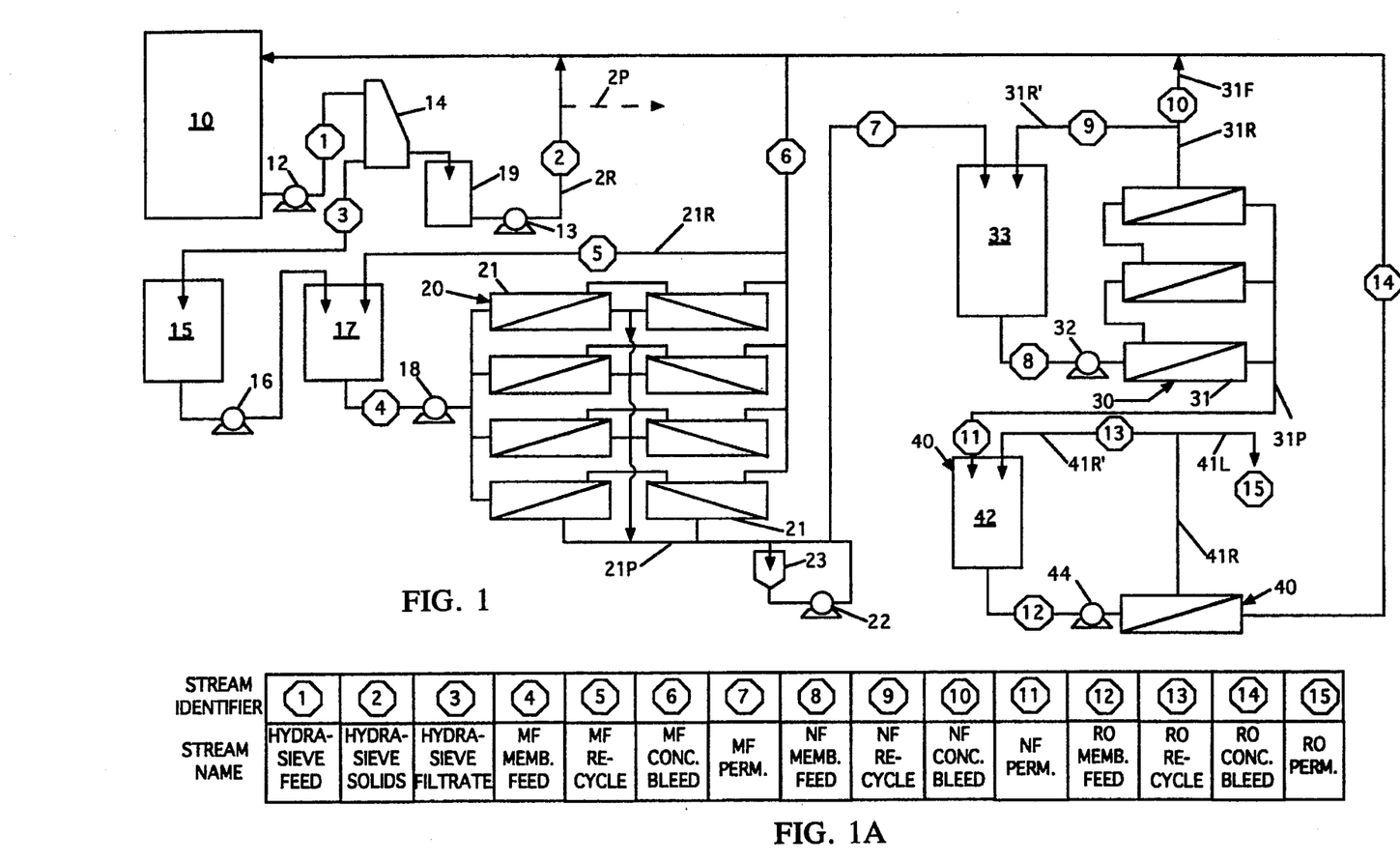
FIG. 1A is a process flow sheet of the process which may be operated either in a batch mode or in a continuous mode depending upon the particular make-up of biomass in the fermentor broth and the economic conditions to be met.

Referring now to FIG. 1 there is shown a flowsheet of a system which recovers lactic acid from corn or sweet sorghum, either of which provides the "right" grain mash. A benefit from corn mash, in particular (used in both the batch and continuous operations described herebelow), is that it generates a broth which is gentle on the surface of a UF membrane. The choice of the "right" strain or mixture of strains of cells which consume sucrose, glucose or fructose, provides a high productivity of lactic acid until substantially all the nutrient in the broth is converted to lactic acid. There are at least three zones of membrane-containing modules in series, namely (i) a UF zone indicated generally by reference numeral 20; (ii) a NF zone 30; and (iii) a RO zone 40, each zone able to separate all forms of lactic acid from a stream flowed into that zone. Despite the stated high selectivity of membranes in each zone, the cost of this fermentation-based process will make it uncompetitive if the productivity of the cells is low.

Batch Fermentation Operation:

Heated, saccharified corn mash containing about 28% by wt total solids, 30% by volume of thin stillage and glucoamylase is flowed into a sterile fermentor 10 where it is diluted with equal parts by wt of thins stillage and deionized water. For example, 26.4 L (100 gal) of corn mash 13.2 containing 7.92 L (30 gal) of thin stillage is diluted with 3.2 L (50 gal) of water and 13.2 L (50 gal) of thin stillage. To the corn mash now containing about 15% by wt total solids is added from about 0.05% to 0.5%, preferably 0.2% by wt of yeast extract (7.71 Kg/264 L or 17 lb per 1000 gal mash), the pH is adjusted to 7.5 with ammonium hydroxide and the temperature adjusted to 55° C. From 0.066 to about 0.528 L (0.25 to about 2 gal), preferably from 0.132 to 0.264 L (0.5–1 gal) of protease is added (to 264 L or 1000 gal of mash), and the mash is allowed to 'age' until the pH is lowered to within the range from about 6.5 to 7.0, preferably 6.8, and the mash is sterilized for at least an hour. The sterile mash is then cooled to 38° C. and inoculated with a high-yielding culture of Lactobacilli, along with addition of from about 0.2 to 1 liter, preferably about 0.4 to 0.8 liter of glucoamylase per 264 L mash. The fermentation is allowed to proceed at a temperature controlled in the range from 36°–42° C., and a pH of about 5 until the concentration of lactic acid reaches the maximum, and the pH in the range from 4.0 to 4.5 does not decrease.

In this batch process, essentially all the bioconvertible sugars are converted at the end of the fermentation, and most of the cells are inactivated when the overall concentration of lactic acid in the fermentor exceeds about 8% despite addition of $NH_4OH$ for pH control.

We have found that cell growth is best when overall concentration of lactic acid (with pH control) is about 5%. Therefore, the batch process suffers relative to the continuous process, described below, in which the lactic acid concentration is preferably not permitted to rise above about 5%, at which the microorganisms thrive. Recycling heavies to the fermentor is not productive.

The fermented broth is pumped by pump 12 from the fermentor 10 through conduit 1 into a Hydrosieve 14 having a mesh size in the range from about 20 µm to 500 µm, preferably 125 µm, to remove suspended 'heavy solids' large enough to interfere with UF filtration of the stream 1. Screened broth is withdrawn through conduit 3 and flowed into a first broth holding tank 15 from which the broth is pumped by pump 16 into a second broth holding tank 17, each tank being maintained at about the same temperature as the fermentor. Solids retained on the screen of the Hydrosieve are sloughed off into solids holding tank 19 from which they are pumped by pump 13, through conduit 2P, shown in phantom (dashed) outline, and dried for animal feed.

From the second tank 17 the broth is pumped through conduit 4 by pump 18 at a pressure in the range from 445–790 kPa (50–100 psig), preferably about 585 kPa (70 psig), into a bank of UF modules 21 arranged in series-parallel. It is critical that the pressure generated in pumps 16 and 18 be low enough so as not to kill the microorganisms, or at least not to kill more than 25% of them, preferably less than 10%, and most preferably less than 5%, or the rate at which the CFU/ml in the fermentor decreases will vitiate the economics of the process.

The permeate flows out of the modules 21 through conduit 21P into a UF permeate holding tank 23, and the retentate flows out of conduit 21R to be returned to the second broth tank 17 which is found to be more expedient than returning it directly to the fermentor 10. A portion of the stream 21R' is purged from the system, as required. The pressure in the conduit 21R is typically about 69 kPa (10 psig) lower than the pressure of the incoming stream to the UF modules, and the pressure in the conduit 21P is typically much lower, about 140 to 280 kPa (20–40 psig) lower. It is found that at a fluid velocity in the range of from about 5–10 meters/sec over the surface of the semi-permeable membrane, there is essentially no build-up of sediment on the surface, that is the silt index is<5, as conventionally measured. Though a higher velocity may be used, there is no significant decrease in silting and no economic incentive for doing so. Under typical conditions the recovery of lactic acid in the UF zone is about 3%.

The NF retentate flowing thorough conduit 31R, is essentially free from suspended solids, but contains from 10% to 30% soluble solids having a mol wt in the range>150 Daltons, but<$2\times10^5$ Daltons. The term "essentially free" refers to less than 5% by wt, preferably less than 3% by wt, and most preferably less than 1% by wt of suspended solids in the UF permeate. The concentration of the higher mol wt solids depends upon how effectively these solids have been removed in the preceding UF step. A portion 31F of the NF retentate 31R is returned to the fermentor 10, and the remaining recycled through conduit 31F to NF-holding tank 33.

Figure 2A:
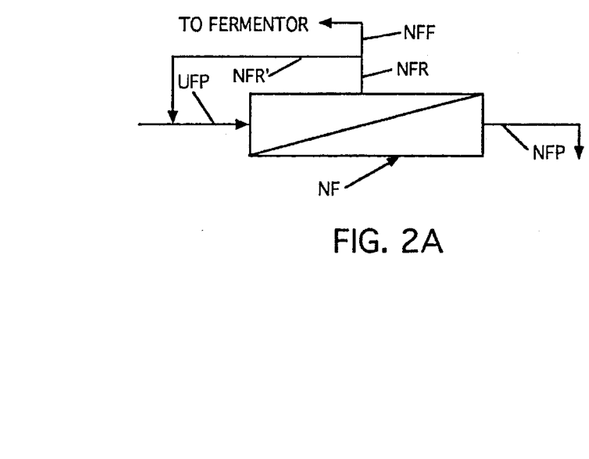
FIG. 2A is a detailed schematic view of a single stage NF zone in which a single module is used.

UF permeate from the UF permeate holding tank 23 is withdrawn by pump 22 and flowed through conduit 7 into NF-feed holding tank 33 in the NF zone 30. Pump 32 withdraws NF feed from the tank 33 and flows the NF feed through conduit 8 into a bank of single stage (a detail is illustrated in FIG. 2A) NF spiral flow modules 31 connected in parallel. The pressure is preferably in the range from 1480 to 2860 kPa (200–400 psig), preferably from about 1725 to 2170 kPa (250–300 psig). The recovery of lactic acid in the NF zone is about 25% under typical process conditions. NF permeate is withdrawn through conduit 31P and flowed into a RO-feed tank 42 in the RO zone 40.

RO-feed from the RO holding tank 42 is withdrawn and pumped by pump 44 through conduit 43 into RO module 41 under pressure in the range from about 4235–7000 kPa (600–1000 psig), preferably from 5270–5960 kPa (750–850 psig) to be separated into a RO-permeate stream of RO-water which is returned to the fermentor through conduit 41P. RO-retentate which is flowed through conduit 41R contains product lactic acid, and a portion of the stream 41R is withdrawn through conduit 41L, while the remaining 41R' is recycled to the RO-feed tank. The recovery of lactic acid in the RO zone is about 90% under typical process conditions.

From the foregoing it will now be evident that the batch fermentation process for separating essentially pure lactic acid comprises, confining a carbohydrate substrate containing fermentable sugars at a temperature in the range from about 20° C. to 50° C. in a batch fermentor in the substantial absence of oxygen and in contact with a Lactobacillus adapted to convert the sugars into a broth containing from 2–5% by wt lactic acid, with minor amounts<1% by wt each, of acetic acid, ethanol and concurrently produced by-products, wherein the lactic acid concentration is measured as lactic acid in equilibrium with lactate anions and hydrogen cations, but in the absence of cations generated by an added nitrogen-containing base; fermenting the fermentable sugars while maintaining the pH in the range from 4.0 to 5.5, preferably 4.5 to 5.0, by adding the nitrogen-containing base which forms a salt soluble in the broth, until the fermentation is self-terminated when the sugar content of the broth is exhausted and the concentration of lactic acid including lactate is in the range from about 8 to 15%; flowing broth from the batch fermentor at a velocity in excess of 3 meters/sec, preferably at from 5–10 m/sec, through a UF tubular membrane module, and returning UF retentate to the fermentor; thereafter flowing the UF permeate to a NF membrane module, withdrawing a NF permeate in which the lactic acid concentration is in the range from 5% to 15%, typically from 5–12%, and returning the retentate to the fermentor; then flowing the NF permeate to a RO membrane, recycling the permeate from the RO membrane to the fermentor, and recovering a retentate rich in lactic acid.

If desired, ammonium lactate generated by addition of $NH_4OH$ (ammonium hydroxide) to maintain the pH in the desired range, is converted to lactic acid by ion exchange with a suitable ion exchange medium.

Continuous Fermentation Operation

Referring now to the continuous process, the charge to the fermentor is prepared as before and the fermentation is allowed to proceed until the HPLC concentration of lactic acid is in the range from 3 to 4.5% when $NH_4OH$ is added to lower the pH into the range from 4.5 to 5.5. This pH is maintained continuously as fermented broth is withdrawn by pump 12 and flowed over the Hydrosieve. Heavy solids retained on the screen of the Hydrosieve are sloughed off into solids holding tank 19 from which they are pumped by pump 13, through conduit 2, and returned to the fermentor 10 through conduit 2R, since the sieve-retained solids contain much bioconvertible sugar.

Because there is a progressive build-up of insoluble solids which are not ingestible by the microorganisms in the fermentor, these solids are periodically purged from the system through conduit 2P. This purge stream 2P, whether from a batch fermentor or a continuous fermentor,is so rich in solids, both insolubles and dissolved, that it may be conventionally dried in a drying zone to produce a low-cost animal nutrient, particularly for dairy cattle, chickens and fish. The amount purged depends upon the CFU/ml in the fermentor and other operating parameters of the process.

As in the batch process, broth essentially freed from heavy solids is held in second tank 17 and then flowed through conduit 4 by pump 18 into the bank of UF modules 21 arranged in series-parallel, and the UF permeate flowed into tank 23.

Because the UF retentate has been substantially stripped of its relatively low mol wt dissolved solids, but contains essentially all live cells and 'heavies' (mol wt>$2\times10^5$ Daltons) in an amount from 25% to 40% by weight, which includes unmetabolized sugars, substantially all the UF retentate is returned to the fermentor, which thus operates as an efficient cell-recycle fermentor.

In a manner analogous to that described above for the batch process, the UF permeate 21P is flowed to the NF zone 30 where it is separated into a NF retentate 31R, a portion 31F of which is returned to the fermentor 10, and the remaining recycled to NF-holding tank 33; and the NF permeate is flowed to the RO-holding tank 42 and separated into product lactic acid and RO water.

As described above, the substantially continuous fermentation process for separating essentially pure lactic acid comprises, flowing fermented broth from an anaerobic cell-recycle fermentor at a velocity in excess of 3 m/sec through a UF tubular membrane module, and returning UF retentate to the fermentor without killing more than 25% of the live cells in the recycle stream; continuously adding a nitrogen-containing base which will form a soluble lactate so as to maintain the pH in the range from 4.5 to 5.5; withdrawing fermented broth from the fermentor continuously to deplete the lactic acid content of the fermentor at substantially the same rate as lactic acid is formed; and, thereafter flowing a UF permeate essentially free from suspended solids, to a NF membrane module; then flowing the NF permeate to a RO membrane, and recycling the retentates from the NF and RO modules to the fermentor, so that the membrane modules in series provide excellent recovery rates for essentially pure lactic acid.

Essentially pure lactic acid, at least 90% pure, the remainder being mainly acetic acid, is recovered if the mash is not diluted with corn thin stillage or steep water. If either a thin stillage or steep water stream is added to the fermenting mash for the new-found nutrient value of either stream, glycerol present in the stream is an additional contaminant, though it is present in a lesser amount than is the acetic acid.

The continuous fermentor is turned over in the range from once every hour to about once every three hours (turnover is 1 per 1–3 hr). The rate at which the fermentor is turned over will depend upon the size of the fermentor, the particular mash being fermented, the degree of control required to be exercised in the process, the specific types of Lactobacilli used, and other processing factors.

Since cells of *L. casei, L. delbrueckii, L. acidophilus, L. bulgaricus* and other similar cells are rod-like in shape, having a diameter of about 0.5 μm and a length of from ≈2 μm–5 μm, a UF membrane having a pore size no larger than 0.375 μm is used, preferably 0.2 μm, but not smaller than 0.1 μm.

Grains, preferably those known to give a high yield of lactic acid such as corn and sweet sorghum, are fermented in the presence of a homofermentative Lactobacillus strain particularly well-adapted to thrive in an acidic environment. The choice of grain is not critical except with respect to its net yield of lactic acid, provided the grain, upon steam jet cooking in the presence of an enzyme, followed by saccharification with another enzyme, generates mainly sugars with 6 carbon atoms ("6-C sugars").

The process of this invention uses a UF system including at least one UF module in a first filtration step to remove a major portion of soluble proteins along with the insolubles at such a high recovery that the permeate produced may be directly filtered in a NF module. "Recovery" is defined as the percent by volume (vol %) of permeate removed, based on 100 volumes of feed to the MF or UF system during the period it is in operation.

It is critical in this step-wise filtration process that the permeate recovery be at least 50% in each filtration step, most particularly in the first step comprising ultrafiltering the thin stillage. It will be appreciated that the higher the permeate recovery in the first step, the higher the recovery of lactic acid in the overall process. More specifically, it will be appreciated that since there is essentially no rejection (less than about 1% for lactic acid) a permeate recovery of 80% in the first step results in an 80% yield of lactic acid. Stated differently, for 1000 gallons (gal) of broth containing 1.5% lactic acid, the yield is 80 gal of MF and/or UF permeate containing 1.5% lactic acid. An equal conc of lactic acid leaves with the UF retentate.

Further, if 26.4 L (100 gal) of MF and/or UF permeate containing only 1% lactic acid is flowed to the second step, namely nanofiltration ("NF"), in the membrane separation process carried out in the membrane means used herein, then if 19.8 L (75 gal) of permeate are recovered (75% permeate recovery), the rejection of lactic acid is 25%, and the conc of lactic acid in the NF permeate is 0.75%.

If in a final step, namely the reverse osmosis ("RO") step in this invention, the permeate recovery was as high as 90%, then the overall permeate recovery for the process would be the product of the individual permeate recoveries in each separation step. If, as is desirable, the permeate recovery in the UF first step is as high as 80%, in the NF second step is as high as 75%, and in the RO third step is as high as 90%, overall permeate recovery is 0.8×0.75×0.9=0.54.

To produce the required high yield of lactic acid we use a conventional cell-recycle fermentor operating at relatively low pH we avoid without neutralizing most of the lactic acid being generated, yet maintain thriving cells. We recycle these live cells to the fermentor after the broth is filtered in cross-flow microfiltration or ultrafiltration modules without first centrifuging the broth. The effective operation of the process relies on maintaining a relatively high temperature and high enough flow velocities over the membranes in each module to minimize fouling of the surfaces, yet not damage them, so that they are clean enough to provide unexpectedly high efficiency for a long period of time. It is because the live cells are only briefly exposed to cell-damaging conditions of filtering and recycling the broth in the first stage, that the cells escape being killed.

Continuous fermentation of the broth in the recycle-fermentor avoids taking the time necessary to grow cells from an initial low concentration once steady state has been reached. At steady state, Bailey et al in U.S. Pat. No. 4,771,001, disclosed that a concentration of cells up to 100 grams per liter dry weight may be reached which cannot be reached in a batch fermentation. This results in a greater rate of lactic acid production per unit volume of fermenter than is obtainable in a batch reactor; and, because the fermentation is continuous, broth is pumped for continuous purification operations without the need for holding tanks. If desired, the purification may be semi-continuous or batch, with holding tanks, but it is evident that, if operated for long periods, there is no down time associated with cleaning and sterilizing the fermentor, and the continuous process will be preferred.

Referring now to FIG. 2A there is schematically shown a detail of a standard, single stage NF zone with a single module in which a UF peremate UFP is separated into a NF permeate NFP and a NF retentate NFR, a portion of which NFF is returned to the fermentor, and the remaining portion NFR' recycled to the incoming UFP. It will be appreciated that, though only a single module is shown, multiple modules may be used in parallel.

Figure 2B:
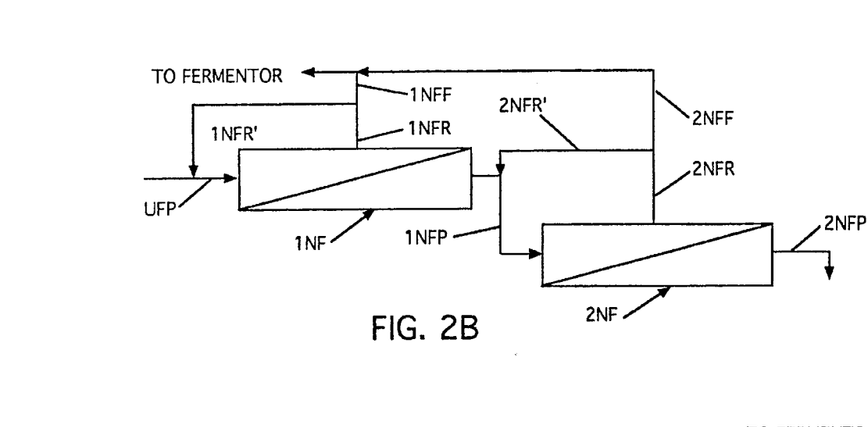
FIG. 2B is a detailed schematic view of a two stage NF zone in which at least two modules are used.

In FIG. 2B there is shown a two stage NF zone with a primary NF module 1NF and a secondary NF module 2NF, connected as shown in series so that UF permeate UFP is separated into primary retentate 1NFR and primary permeate 1NFP. The permeate 1NFP is flowed to 2NF, and portions of the retentates 1NFR and 2NFR are returned to the fermentor through conduits 1NFF and 2NFF respectively, with the remainder being recycled through 1NFR' and 2NFR' respectively to the incoming UFP and 1NFP. The NF permeate from the secondary NF module leaves through 2NFP to a RO module (not shown). As before multiple primary and secondary modules may be used, connected as shown.

Figure 2C:
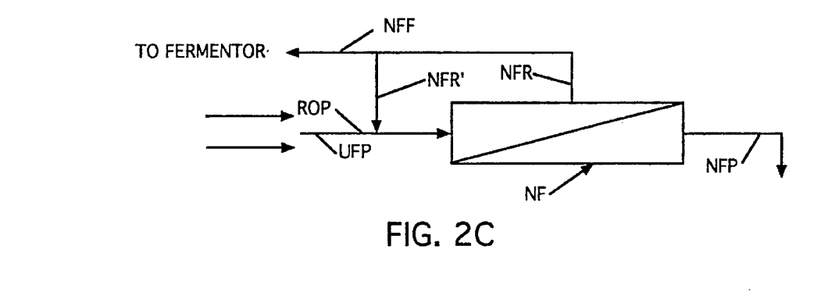
FIG. 2C is a detailed schematic view of a diafiltration system to improve recovery of the lactic acid.

FIG. 2C schematically illustrates operation of a single NF module in a diafiltration mode wherein UF permeate UFP is flowed to the NF module and separated into NF permeate NFP, and NF retentate NFR streams. The NFP from the secondary NF module leaves through 2NFP to a RO module (not shown) from which a portion of the RO permeate is returned to the NF zone. A portion of the NFR is returned to the fermentor through NFF and the remainder NFR' is recycled to the incoming UFP. The UFP is further diluted with a portion of the RO permeate returned to the NF zone, the net effect being to improve recovery of the lactic acid from the NF retentate.

Protease Added as Nutrient

The effect of using protease instead of a conventional phosphate buffer in the production of lactic acid by a particular strain of cells was obtained by comparing standard fermentations of a charge of saccharified corn mash. The charge for a 264 L (1000 gal) fermentor is made up as described hereinabove with thin stillage and 0.2% of yeast extract. In the first fermentation 0.45% phosphate buffer was used. In the second fermentation, the phosphate buffer was replaced with 0.5 gal of protease. In each case the fermentation was initiated at pH 8 and thereafter controlled in the range from pH 5.1–5.3, attempting to maintain pH 5.2 throughout, by addition of ammonium hydroxide. Readings were made with samples of broth taken at predetermined intervals and centrifuged to provide broth which was then filtered. The filtrate was then tested for glucose and lactic acid by HPLC analysis.

Figure 3:
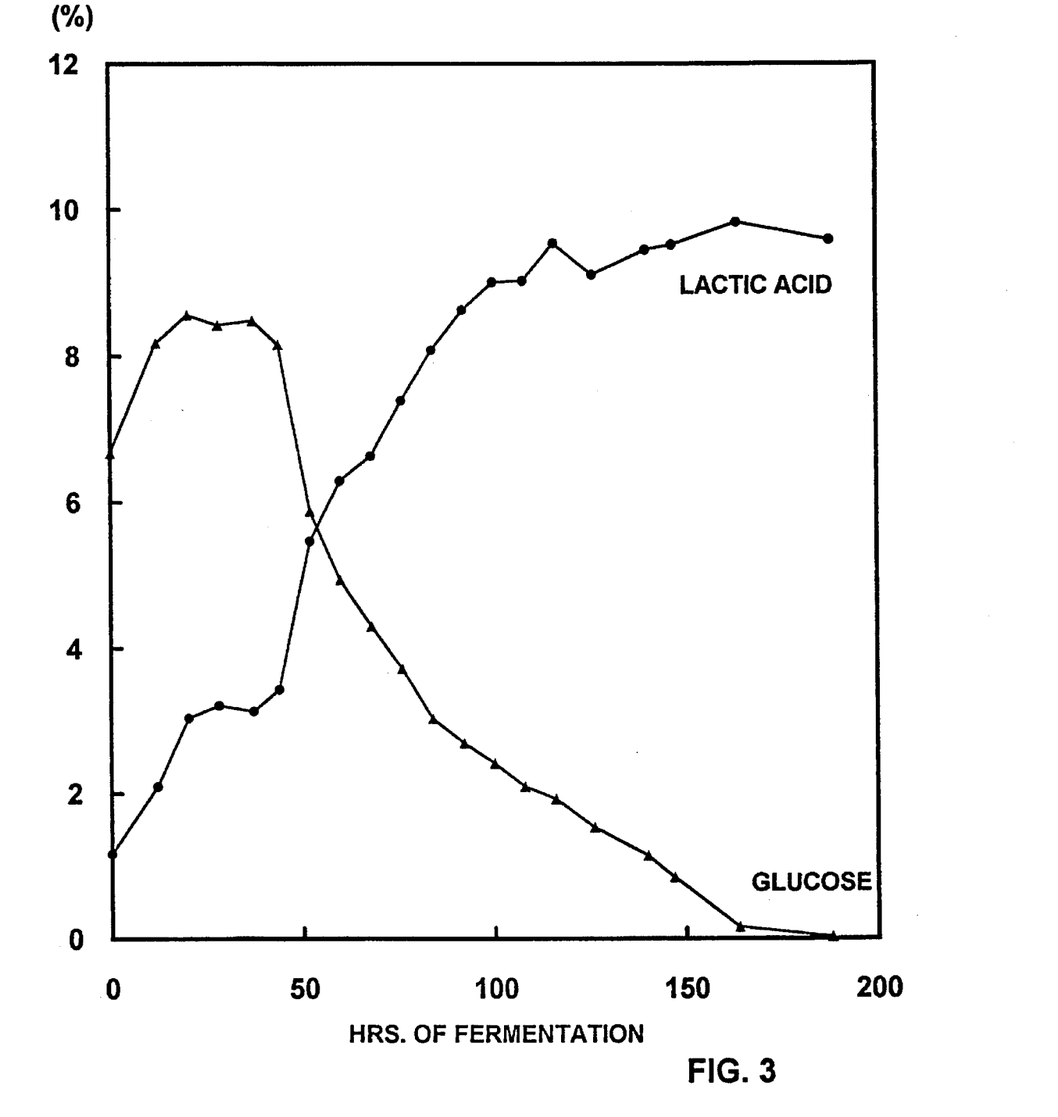
FIG. 3 is a fermentation profile of a batch fermentor buffered with a conventional phosphate buffer medium, and containing no added enzyme, specific for the hydrolytic breakdown of proteins, added to the fermenting biomass.
Figure 4:
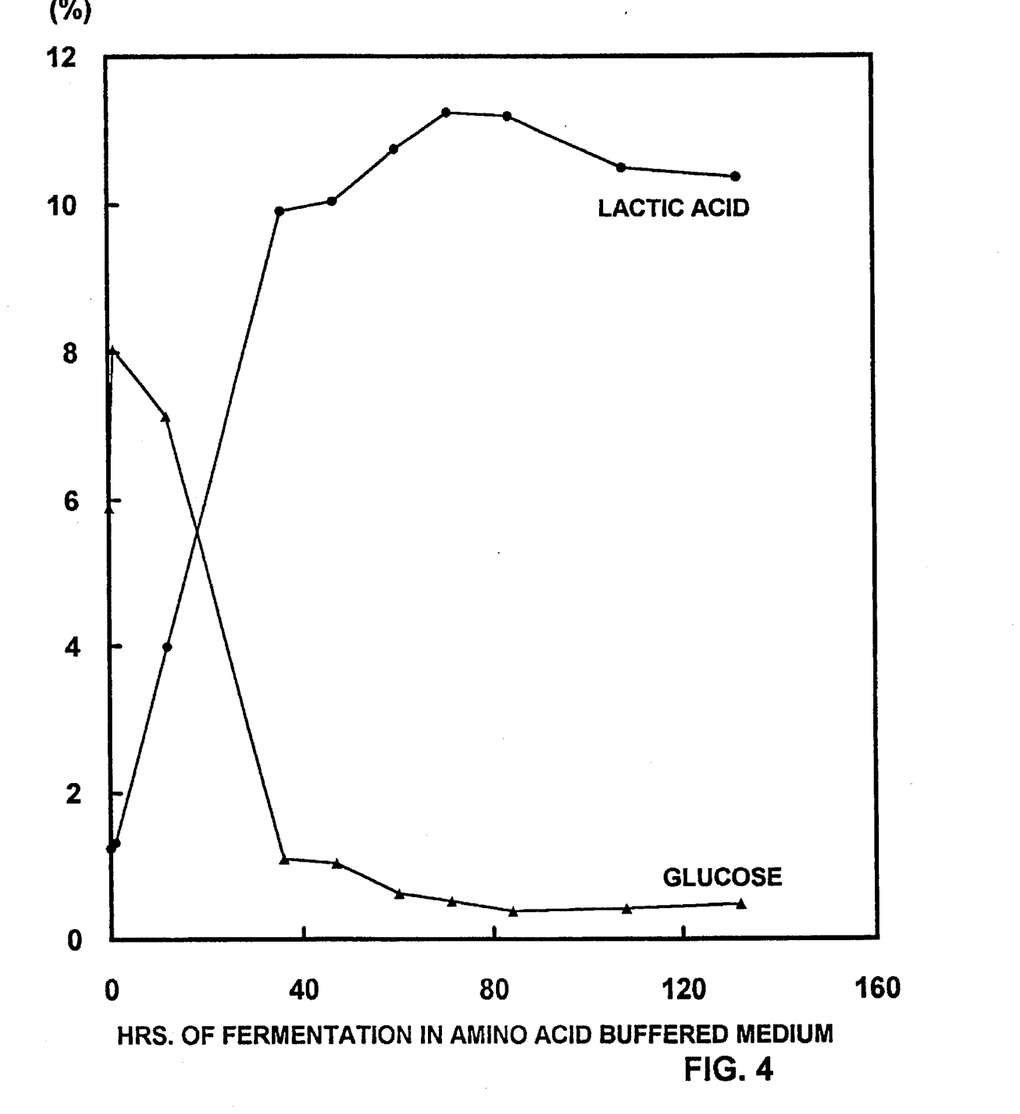
FIG. 4 is a fermentation profile of a batch fermentor with protease added to provide a boost in lactic acid production, the broth being buffered with amino acids produced by the in situ hydrolytic breakdown of proteins present in the broth, by the added protease.

Referring to FIGS. 3 and 4 there is shown, in each, a fermentation profile plotting the glucose and lactic acid concentrations on the left and right ordinates respectively, against the number of hours of fermentation with a particular strain of cells.

In FIG. 3 it is evident that the concentration of lactic acid does not reach its maximum of 9.5% until 120 hr of fermentation, and substantially all the glucose is converted at the end of about 160 hr.

In FIG. 4 it is evident that the concentration of lactic acid exceeds 9.5% at about 72 hr, then proceeds to a maximum of about 11.2% soon thereafter when essentially all the glucose is converted.

A comparison of the results in the FIGS. 3 and 4 demonstrates that replacing a phosphate buffer with protease in a lactic acid fermentation is not only unexpectedly efficient because it proceeds faster, but also more productive, since a higher concentration of lactic acid is obtained at the end of the fermentation. It is seen that the use of protease improves the conc of lactic acid by about 18% and this improvement is obtained over a period which is about 60% shorter than the conventional method.

The membranes used in each zone are made of conventional membrane material whether inorganic, organic, or, mixed inorganic and organic. Typical inorganic materials include glasses, ceramics, cermets, metals and the like. Ceramic membranes which are preferred for the UF zone, may be made, for example, as described in U.S. Pat. Nos. 4,692,354 to Asaeda et al (class 472/ subclass 244), 4,562,021 to Alary et al (class 264/subclass 43), and others. The organic materials which are preferred for the NF and RO zones, are typically polymers, whether isotropic, or anisotropic with a thin layer or "skin" on either the bore side or the shell side of the fibers. Preferred materials for fibers are polysulfones, poly(styrenes), including styrene-containing copolymers such as acrylo-nitrile-styrene, butadiene-styrene and styrene-vinylbenzylhalide copolymers, polycarbonates, cellulosic polymers, polypropylene, poly(vinyl chloride), poly(ethylene terephthalate), and the like disclosed in U.S. Pat. No. 4,230,463 the disclosure of which is incorporated by reference thereto as if fully set forth herein.

The membranes are chosen with a view to performing their desired function and are non-randomly oriented in each module, so that the flow of feed through the module is in cross-flow. Typically, a fermentor is operatively connected with a UF zone having a variable module, multi-tube membrane unit of Zenon Z8 modules with ceramic membranes such as Ceramem and Alcoa 1P19, or with HSC or TAM organic membranes. Each module contains 8 1.83 m long by 2.22 cm diameter tubes connected in series to provide a membrane area of 0.975 m²/module. The modules themselves are connected in parallel with the concentrate recycle to the fermentor.

One skilled in the art will appreciate that because a NF membrane is semipermeable, higher pressures are required to produce an NF permeate economically, than are used to produce UF permeate in the UF zone. Preferred NF membranes are NF 40 and NF 70 made by Filmtec and Desal 5 made by Desalination Corp.

The requirement of high pressure is still greater in the RO zone because the aqueous NF premeate feed must be at a pressure above the osmotic pressure of the dissolved substances in the water. Because an RO membrane can effectively remove low mol wt molecules<50 Daltons, and also ions from water, the same RO membranes which are commonly used to demineralize water (e.g. for pretreating boiler feedwater, and recovering potable water from brackish water or sea water) may be used.

The following RO membranes provide good service:

| Filmtec BW-30; | Filmtec SW-30; | Filmtec SW-30HR |
|---|---|---|
| UOP RO membrane | Desal RO membrane | Osmonics RO membrane |
| Nitto RO membrane. | | |

Having thus provided a general discussion, described the overall process in detail and illustrated the invention with specific examples of the best mode of carrying out the process, it will be evident that the invention has provided an effective and economic solution to a difficult problem. It is therefore to be understood that no undue restrictions are to be imposed by reason of the specific embodiments illustrated and discussed, and particularly that the invention is not restricted to a slavish adherence to the details set forth herein.

We claim:

1. A fermentation process for producing lactic acid, comprising, fermenting a carbohydrate substrate containing saccharified mash of grain, rich in free sugars, in contact with strains of rod-like cells of Lactobacillus in a cell-recycle fermentation zone, to obtain a broth containing at least 5 gm of lactic acid per 100 ml of broth;

maintaining a concentration of cells greater than $5 \times 10^9$ CFU/ml in said broth at a temperature in the range from about 20° C. to 50° C.; a pH in the range from 4.5 to 5.5 which maintains lactate anions and hydrogen cations in equilibrium under extant conditions; and, a pressure in the range from above 1 atm up to 10 atm which is ineffective to deleteriously affect said cells and the rate at which said free sugars are converted by them;

withdrawing a fermentor effluent stream from said cell-recycle fermentation zone and flowing said effluent stream through an ultrafiltration ("UF") zone having tubular membranes therein, at a fluid velocity of at least 3 m/sec, sufficient to scrub membrane surfaces in said UF zone and maintain their efficiency, said UF zone having at least one cross-flow UF module containing a UF membrane having a pore size in the range from 0.1 µm to 0.375 µm to minimize endwise insertion of said rod-like cells in pores of said membrane;

withdrawing a cell-rich UF retentate containing less than 5% by weight lactic acid from said UF zone, along with (i) substantially all cells leaving said cell-recycle fermentation zone in said fermentor effluent stream, (ii) suspended solids >0.3 µm, and (iii) 'heavies' present in said broth; recycling said cell-rich UF retentate to said cell-recycle fermentation zone at a pressure and temperature conducive to maintaining said cells alive, said UF retentate containing more than 75% of live cells leaving said cell-recycle fermentation zone; withdrawing an essentially cell-free UF permeate from said UF zone with a recovery of at least 50%, and flowing said UF permeate to a nanofiltration ("NF") zone having a NF membrane essentially impermeable to molecules having a molecular weight >150 Daltons and permeable to ionized and non-ionized molecules having a mol wt <150 Daltons, in cross-flow, at a pressure and temperature chosen to provide a desirable flux;

withdrawing from said NF zone, a NF retentate containing essentially all soluble solids having a mol wt >150 Daltons and returning said NF retentate to said cell-recycle fermentation zone to be fermented;

withdrawing from said NF zone, a NF permeate with a recovery of at least 50% lactic acid, said NF permeate containing at least 70% of lactic acid present in said UF permeate, said NF permeate being essentially free of dissolved solids and multivalent ions having a molecular weight >150 Daltons and flowing said NF permeate to a reverse osmosis (RO) zone having a module with an RO membrane permeable to non-ionized molecules having a molecular weight <50 Daltons, in cross-flow at a pressure and temperature chosen to provide a desirable flux;

withdrawing a RO permeate from said RO membrane zone with a recovery of at least 50% and flowing said RO permeate to said cell-recycle fermentation zone or to boiler water make-up feed; and, withdrawing a RO retentate from said RO membrane zone; whereby said RO retentate contains at least 90% of lactic acid and glycerol present in said NF permeate, and said RO permeate is water essentially free of dissolved solids and organic compounds having a molecular weight >50.

2. The process of claim 1 wherein said grain is corn and/or sweet sorghum, and said strains of Lactobacillus include *L. casei, L. delbrueckii, L. xylosus, L. plantarum, L. acidophilus*, and *L. bulgaricus* present in a concentration in the range from $5 \times 10^9$ to $5 \times 10^{10}$ CFU/ml, said broth contains from 10–15 gm of lactic acid per 100 gm of said broth, said cell-recycle fermentation zone is operated at a temperature in the range from about 30° C. to 40° C., and said UF membrane pore size is in the range from 0.1 μm–0.2 μm.

3. The process of claim 2 wherein said carbohydrate substrate is a saccharified mash of grain, said fluid velocity is in the range from 5 to 30 m/sec, said cell-rich UF retentate contains essentially all cells leaving said tubular UF zone, solid particles >0.2 μm, 'heavies' comprising molecules in the range from 10000–200,000 Daltons, and less than 1% by wt lactic acid.

4. The process of claim 3 wherein, said fluid velocity through said UF membrane is in cross-flow in the range from 5 to 10 m/sec, flow through said NF membrane is in cross-flow, said NF membrane is a spiral wound membrane, said pressure and temperature chosen to provide a desirable flux in said NF zone, is in the range from about 5 atm to 20 atm which fails to damage said NF membrane;

flow through said RO membrane is in cross-flow, said RO membrane is a spiral wound membrane, said pressure and temperature chosen to provide a desirable flux in said RO zone, is in the range from about 25 atm to 60 atm which fails to damage said NF membrane.

5. The process of claim 2, comprising, adding to said saccharified mash an effective amount of an enzyme that catalyzes the hydrolytic breakdown of proteins to generate amino acids and peptides in situ, and at the same time providing an effective buffer action.

6. The process of claim 5 wherein said enzyme is protease.

7. In a process for separating lactic acid from a fermentation broth containing lactic acid produced by a fermentation process comprising contacting a carbohydrate substrate containing fermentable free sugars which are bioconverted to lactic acid and acetic acid in a fermentation zone, the improvement comprising, fermenting said broth by adding to said carbohydrate substrate, a water-soluble nitrogen-containing base favored by said cells and a nutrient present in a minor proportion by weight of said broth, said nutrient being a by-product stream selected from the group consisting of corn thin stillage and steep water, each obtained as a byproduct of a dry milling and a wet milling process, respectively, for the fermentation of saccharified corn mash to produce ethanol;

maintaining a temperature in the range from 20° C. to 50° C. and a pH in the range from 4.5 to 5.5 so as to provide Lactobacillus cells in a super-dense population in excess of $5 \times 10^9$ CFU/ml: and, separating said lactic acid from said broth by sequential filtration in a UF zone, a NF zone and a RO zone, each in cross-flow, and in each of which the recovery of lactic acid in permeate is at least 50%.

8. The process of claim 7 wherein said nutrient is present in an amount from 5% to 35% by weight of said broth in said fermentation zone.

9. The process of claim 8, comprising, adding to said saccharified mash an effective amount of an enzyme that catalyzes the hydrolytic breakdown of proteins to generate amino acids and peptides in situ, and at the same time providing an effective buffer action.

10. The process of claim 9 wherein said enzyme is protease.

11. The process of claim 7 comprising, filtering said broth in said UF zone having at least one module containing a tubular membrane having a pore size greater than 0.1 μm but not greater than 0.375 μm in which UF zone a UF feed of said broth is flowed at a fluid velocity exceeding 3 m/sec under a pressure in the range from 1 atm to 10 atm so as to keep at least 75% of cells in said UF feed alive after passing through said UF zone;

withdrawing an essentially cell-free UF permeate from said UF zone with a recovery of at least 50%, and flowing said UF permeate to a nanofiltration ("NF") zone having a NF membrane essentially impermeable to molecules having a molecular weight >150 Daltons and permeable to ionized and non-ionized molecules having a mol wt <150 Daltons, in cross-flow, at a pressure and temperature chosen to provide a desirable flux;

withdrawing from said NF zone, a NF retentate containing essentially all soluble solids having a mol wt >150 Daltons and returning said NF retentate to said cell-recycle fermentation zone to be fermented;

withdrawing from said NF zone, a NF permeate with a recovery of at least 50% lactic acid, said NF permeate containing at least 70% of lactic acid present in said UF permeate, said NF permeate being essentially free of dissolved solids and multivalent ions having a molecular weight >150 Daltons and flowing said NF permeate to a reverse osmosis (RO) zone having a module with an RO membrane permeable to non-ionized molecules having a molecular weight <50 Daltons, in cross-flow at a pressure and temperature chosen to provide a desirable flux; withdrawing a RO permeate from said RO membrane zone with a recovery of at least 50% and flowing said RO permeate to said cell-recycle fermentation zone or to boiler water make-up feed; and, withdrawing a RO retentate from said RO membrane zone;

whereby said RO retentate contains at least 90% of lactic acid and glycerol present in said NF permeate, and said RO permeate is water essentially free of dissolved solids and organic compounds having a molecular weight >50.

12. A batch fermentation process for preparing lactic acid and separating it in essentially pure form, comprising, confining a carbohydrate substrate containing fermentable sugars at a temperature in the range from about 20° C. to 50° C. in a batch fermentation zone in the substantial absence of oxygen and in contact with a strain of Lactobacillus adapted to convert sugars having six carbon atoms into a broth containing from 2–5% by wt lactic acid, with minor amounts <1% by wt each, of acetic acid, ethanol and concurrently produced by-products, wherein concentration of lactic acid is measured as total lactic acid in equilibrium with all lactate anions and hydrogen cations;

fermenting said fermentable sugars while maintaining the pH in the range from 4.0 to 5.5, by adding a nitrogen-containing base which forms a salt soluble in the broth, until the fermentation is self-terminated when the sugar content of the broth is exhausted and said concentration of lactic acid including lactate ions is in the range from about 8 to 15% by weight;

flowing broth from said batch fermentation zone at a velocity in excess of 3 meters/sec, over the surface of a UF tubular membrane, and returning UF retentate to said fermentation zone;

thereafter flowing UF permeate to a NF membrane module, withdrawing a NF permeate in which said lactic acid concentration is in the range from 5% to 12%, and returning said retentate to said fermentation zone;

then flowing said NF permeate to a RO membrane means, recycling RO permeate from said RO membrane means to said fermentation zone, and recovering said retentate rich in lactic acid.

13. The process of claim 12 wherein said carbohydrate substrate is a saccharified mash of grain, and said strains of Lactobacillus include *L. casei* and *L. delbrueckii* together present in a concentration in the range from $4 \times 10^{10}$ to $5 \times 10^{9}$ CFU/ml, said broth contains from 8–15 gm of lactic acid per 100 gm of said broth, said cell-recycle fermentation zone is operated at a temperature in the range from about 30° C. to 40° C., and said UF membrane pore size is in the range from 0.1 μm–0.2 μm.

14. The process of claim 13 wherein said grain is corn and/or sweet sorghum, said pH is in the range from 4.5 to 5.0, said fluid velocity is in the range from 5 to 50 m/sec, said cell-rich UF retentate contains essentially all cells leaving said tubular UF zone, solid particles >0.2 μm, 'heavies' comprising molecules in the range from 10000–200,000 Daltons, and less than 1% by wt lactic acid.

15. The process of claim 14 wherein, said fluid velocity through said UF membrane is in cross-flow in the range from 5 to 10 m/sec, flow through said NF membrane is in cross-flow, said NF membrane is a spiral wound membrane, said pressure and temperature chosen to provide a desirable flux in said NF zone, is in the range from about 5 atm to 20 atm which fails to damage said NF membrane;

flow through said RO membrane is in cross-flow, said RO membrane is a spiral wound membrane, said pressure and temperature chosen to provide a desirable flux in said RO zone, is in the range from about 25 atm to 60 atm which fails to damage said NF membrane.

16. The process of claim 12 comprising, adding to said saccharified mash, a nutrient in said broth said nutrient being present in a minor proportion by weight of said broth, said nutrient being a by-product stream selected from the group consisting of corn thin stillage and steep water, each obtained in a process chosen from a dry milling and a wet milling process, respectively, for the fermentation of saccharified corn mash to produce ethanol.

17. The process of claim 16 wherein said nutrient is present in an amount from 5% to 35% by weight of said broth in said fermentation-zone.

18. The process of claim 17, comprising, adding to said saccharified mash an effective amount of an enzyme that catalyzes the hydrolytic breakdown of proteins to generate amino acids and peptides in situ, and at the same time providing an effective buffer action.

19. The process of claim 18 wherein said enzyme is protease.

20. The process of claim 19 comprising adding from 0.066 to about 0.528 L of said protease per 264 L of said mash and said mash is 'aged' until said pH is lowered to within the range from about 6.5 to 7.0.

* * * * *